US009172886B2

(12) United States Patent
Nambakam

(10) Patent No.: US 9,172,886 B2
(45) Date of Patent: Oct. 27, 2015

(54) METHOD AND APPARATUS FOR WIRELESSLY SYNCHRONIZING IMAGE SHUTTER OF IMAGE SENSOR AND LIGHT SOURCE

(75) Inventor: Vasudev Nambakam, San Jose, CA (US)

(73) Assignee: Stryker Corporation, Kalamazoo, MI (US)

(*) Notice: Subject to any disclaimer, the term of this patent is extended or adjusted under 35 U.S.C. 154(b) by 519 days.

(21) Appl. No.: 13/578,894

(22) PCT Filed: Mar. 24, 2010

(86) PCT No.: PCT/US2010/000880
§ 371 (c)(1),
(2), (4) Date: Aug. 14, 2012

(87) PCT Pub. No.: WO2011/119134
PCT Pub. Date: Sep. 29, 2011

(65) Prior Publication Data
US 2012/0307029 A1 Dec. 6, 2012

(51) Int. Cl.
*A61B 1/06* (2006.01)
*G02B 23/24* (2006.01)
*H04N 5/225* (2006.01)
(Continued)

(52) U.S. Cl.
CPC .......... *H04N 5/2353* (2013.01); *A61B 1/00016* (2013.01); *A61B 1/045* (2013.01); *A61B 1/0669* (2013.01); *H04N 5/2354* (2013.01); *H04N 7/185* (2013.01); *G02B 23/2484* (2013.01); *H04N 2005/2255* (2013.01)

(58) Field of Classification Search
None
See application file for complete search history.

(56) References Cited

U.S. PATENT DOCUMENTS 4,298,260 A * 11/1981 Takayama ..................... 396/17
7,258,663 B2    8/2007 Doguchi et al.
(Continued)

FOREIGN PATENT DOCUMENTS

GB    2 286 939    8/1995
WO    WO 2010/059179 A1    5/2010

OTHER PUBLICATIONS

International Search Report and Written Opinion of the International Searching Authority issued in International Application No. PCT/US2010/000880 mailed Dec. 14, 2010 (12 pages).
(Continued)

*Primary Examiner* — Michael Teitelbaum
(74) *Attorney, Agent, or Firm* — Flynn, Thiel, Boutell & Tanis, P.C.

(57) ABSTRACT

A method and apparatus for wirelessly synchronizing operation of an image sensor of an endoscopic video camera unit having a wireless transmitter with operation of a portable endoscopic light source unit includes transmitting a message packet with a target camera shutter period, light source target phase/trigger time/OFF time and light source target ON time to the light source unit. The light source unit controls the start time and the ON time for light output by a light source. The video camera unit includes a light detector for detecting the actual light source start time and duration of light output to provide closed-loop feedback. A camera controller ensures synchronization between the shutter period of the image sensor and actual operation of the light source based on the actual phase and actual ON time sensed by the light detector and the previously communicated target phase/trigger time/OFF time and target ON time.

7 Claims, 7 Drawing Sheets

(51) Int. Cl.
*H04N 7/18* (2006.01)
*H04N 5/235* (2006.01)
*A61B 1/00* (2006.01)
*A61B 1/045* (2006.01)

(56) References Cited

U.S. PATENT DOCUMENTS

| | | |
|---|---|---|
| 2005/0075539 A1 | 4/2005 | Schultz |
| 2006/0182431 A1 | 8/2006 | Kobayashi et al. |
| 2008/0139881 A1 | 6/2008 | Cover et al. |
| 2008/0298793 A1 | 12/2008 | Clark |
| 2009/0136225 A1 | 5/2009 | Gai et al. |
| 2009/0214225 A1 | 8/2009 | Nakagawa et al. |
| 2009/0240108 A1* | 9/2009 | Shimizu et al. ............. 600/109 |
| 2009/0292168 A1 | 11/2009 | Farr |
| 2011/0234781 A1* | 9/2011 | Hackel et al. ................ 348/66 |

OTHER PUBLICATIONS

International Preliminary Report on Patentability and Written Opinion of the International Searching Authority, issued in PCT/US2010/000880 dated Sep. 25, 2012 (10 sheets).

* cited by examiner

METHOD AND APPARATUS FOR WIRELESSLY SYNCHRONIZING IMAGE SHUTTER OF IMAGE SENSOR AND LIGHT SOURCE

FIELD OF THE INVENTION

This invention is directed to a method and apparatus for wirelessly synchronizing operation of an endoscopic camera unit with operation of an endoscopic light source unit that is provided with a separate endoscopic device.

BACKGROUND OF THE INVENTION

The remote control of endoscopic devices connected to each other through hard-wired connections is well known for performing surgical procedures. A plurality of devices including cameras, cutting tools, irrigation devices, light sources, and suction devices are connected via a network to a system controller. The system controller is capable of communicating with and controlling the various devices.

An endoscopic system with an irradiated light switching feature is disclosed in U.S. Pat. No. 7,258,663, issued Aug. 21, 2007. An endoscope of the system includes an image sensor incorporated in an insertion unit. The sensitivity of the image sensor can be varied by applying a plurality of pulsating driving signals thereto from a camera controller. The camera controller adjusts the sensitivity of the image sensor according to the type of endoscope employed. A separate light source provides light to a surgical site via a light guide extending through the insertion unit. The light is reflected at the surgical site and received by the image sensor. The insertion unit includes a memory that provides information as to the type of endoscope to the camera controller for the image sensor via a hard-wired connection. Further, a wired connection from a light source controller to the camera controller provides other parameters of the light source.

The '663 patent also discloses utilizing a light level sensor to calculate light output from an average of voltage levels of each video image output signal from the image sensor during one field or interval. This average value can be used to adjust the length of time of light source operation via a hard-wired connection by controlling the amount of time that the light source operates to minimize the amount of heat output from the light source. Light output adjustment is made with a diaphragm control command provided so that an iris diaphragm of the light source is opened or closed in response to the brightness detected by the image sensor. Thus, the intensity of light provided from the light source is automatically adjusted in view of the intensity of light sensed by the image sensor. The feedback arrangement of the '663 patent is provided by the hard-wired connection between the camera controller and the light source controller. The image sensor and light source provide light and sense light via the same insertion unit of an endoscope. Thus, the light source and camera controllers are located adjacent each other, and a hard-wired connection between the controllers is practical.

In some arthroscopic surgical procedures, however, the light source and the camera are provided with separate endoscopic devices. In such instances, providing a hard-wired connection between a camera controller and a light source controller is not practical as movement of the light source relative to the camera would be limited and awkward due to the presence of a connecting cable therebetween. Further, in some procedures, such as ENT procedures, a portable lightweight and compact hand-held light source unit is highly desirable. Further, a wired connection to a camera unit is not practical. Constant output of light by the hand-held light source requires a large battery that results in a heavier light source unit to be manipulated and an undesirable output of heat and thus presents a technical problem.

To reduce the amount of light output and thus energy needed by the portable light source unit, a goal is to synchronize periodic or intermittent operation of the light source with the image shutter of the video camera unit while maintaining sufficient light to obtain video images. The reduction in energy output from the light source increases the battery life of the existing battery. On the other hand, this reduction in light source usage enables the use of a smaller battery and thus a smaller and less heavy portable light source unit that also outputs less heat in operation. The inability to synchronize the video camera unit and the light source unit without a wired connection is a technical problem to be solved by the invention.

SUMMARY OF THE INVENTION

In order to obviate or at least minimize the disadvantages of known arrangements as discussed above, the invention provides wireless communication from a video camera unit to a light source unit for synchronizing an intermittent or periodic light source output with the electronic camera shutter of the video camera unit.

Further, the invention provides a portable wireless light source unit designed with a minimally sized battery for use, for example, in ENT (ear, nose, throat) surgical procedures. The invention is additionally applicable in arthroscopy, wherein different angled endoscope tips present difficulties in providing a camera unit and a light source unit in the same endoscope.

One embodiment of the invention provides a wireless message packet from the camera unit to the light source unit with information or data regarding target phase or time shift for triggering operation of the light source and data providing a length of time for operation of the light source.

In another embodiment, the camera unit includes a photosensor or light detector separate from the image sensor for detecting the exact start time and time of operation that the light source provides light. The information determined by the light detector provides feedback to the camera controller for adjusting the information for the wireless control signals sent to the light source controller, to ensure that light source operation is synchronized with the electronic camera shutter of the video camera unit. The feedback provides a closed-loop system ensuring that operation of the light source is directly synchronized with the camera shutter of the video camera unit. The arrangement minimizes the usage of the battery for the light source unit, and thus reduces size and weight requirements for the battery.

The invention additionally pertains to a method of providing a wireless signal from a camera controller of a video camera unit to a light source controller of a separate portable endoscopic light source unit. A periodic message packet in the wireless signal received by the light source unit controls the start time of the light source and the length of time the light source provides illumination to a surgical site. Thus, light source operation is typically controlled, rather than the shutter speed of the image sensor, which generally remains constant.

In another embodiment, the light source controller provides an additional predetermined phase shift or time delay in starting lamp or light emitting diode operation. Instead of simply operating at a target phase provided by the wireless signal from the camera controller, the additional phase shift corresponds to an individual data bit that is then detected by a light detector of the video camera unit. For example, the beginning and the end of a light source output may be time shifted forward by two microseconds or instead delayed by two microseconds to provide a bit signal of "one". The beginning and the end of the light source output may both be shifted forward or delayed one microsecond to provide a "zero" bit signal. The overall length of time that the light source provides a light output does not change.

In this data transfer arrangement, the shifting at the beginning and the end of a light output provides various information to the camera controller with regard to the battery powered light source. For instance, the remaining battery life of the light source battery can be provided to the camera controller, the amount of time the LEDs have been driven and the type of and specifications for LEDs or lamp components provided for the light source.

In another embodiment of the invention, the camera controller transmits a wireless signal to the light source controller for synchronizing the camera and light source unit. The light source control unit includes an RF transmitter for then transmitting a wireless RF signal to an RF receiver of the video camera unit. This arrangement does not require a light detector for determining the phase and length of time of the light source output, as digital signal packets and RF transmitter/receiver pairs are provided instead. Data with regard to the light source unit is provided with a return signal transmitted from the RF transmitter of the light source unit to the RF receiver of the video camera unit.

DETAILED DESCRIPTION OF THE INVENTION

Figure 1:
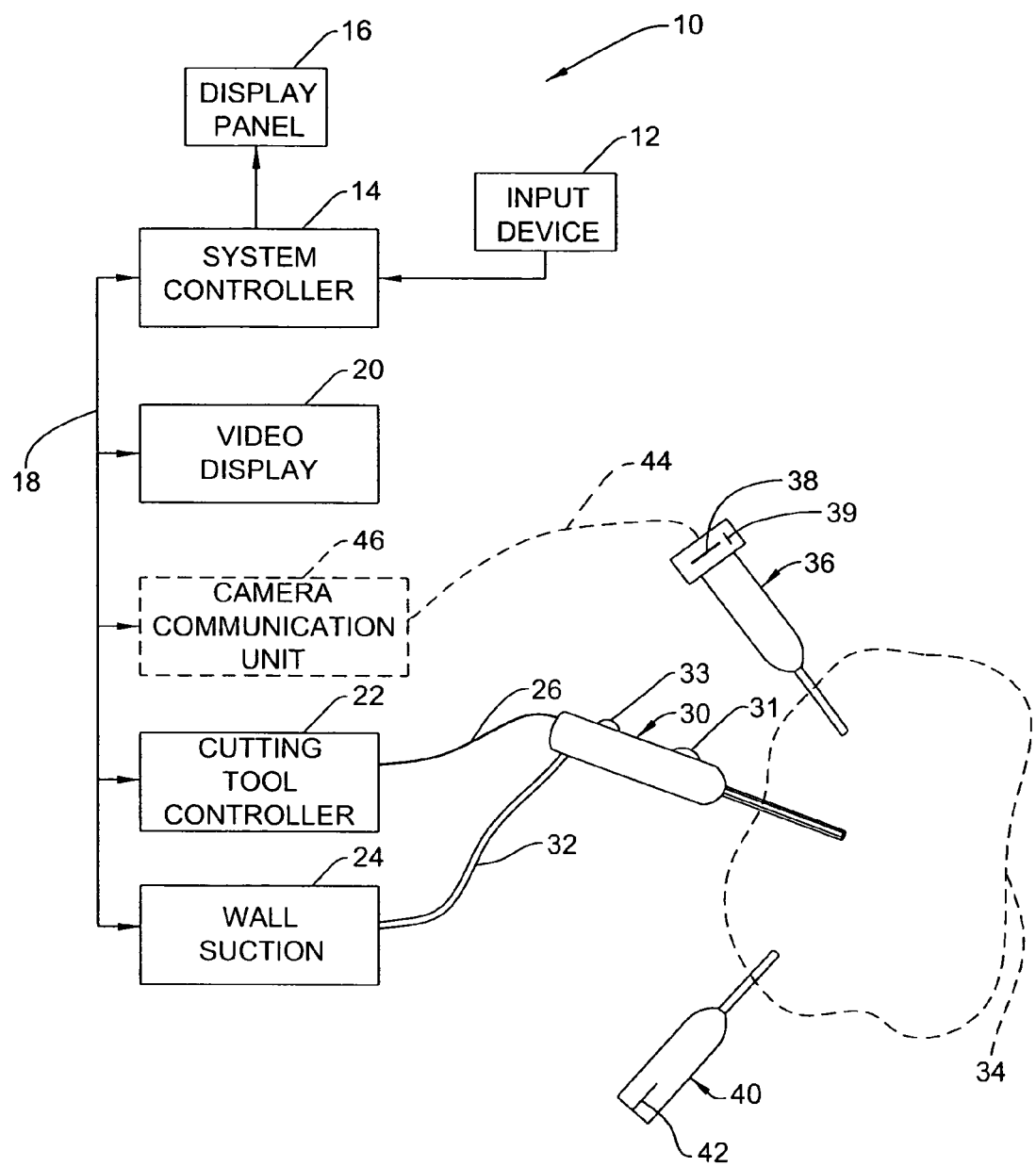
FIG. 1 shows an operating room system including a portable endoscopic video camera unit and a portable light source unit.

FIG. 1 shows an operating room control system 10 including an input device 12 for selectively providing input signals to a system controller 14. The system controller 14 is connected to a display panel 16. The system controller 14 is also connected via a network 18 to a plurality of surgical devices including a video display 20.

In FIG. 1, the system controller 14 is connected via the network 18 to a cutting tool controller 22 and a wall suction unit 24. A control signal line 26 connects the cutting tool controller 22 to an endoscopic cutting tool 30 having an on/off switch 31. Suction tubing 32 connected at one end to the wall suction unit 24 provides a suction flow path to the endoscopic cutting tool 30. The cutting tool 30 is a shaver or other cutting device and has a suction control activator 33 to remove tissue and debris from a surgical site 34.

FIG. 1 shows a wireless portable endoscopic video camera unit 36 having antenna arrangements 38, 39. The endoscopic wireless video camera unit 36 wirelessly transmits non-video light source control signals via antenna arrangement 38 and transmits video signals via antenna arrangement 39.

Portable light source unit 40 shown in FIG. 1 includes a receiving antenna arrangement 42 for receiving wireless non-video signals from the endoscopic video camera unit 36.

Figure 2:
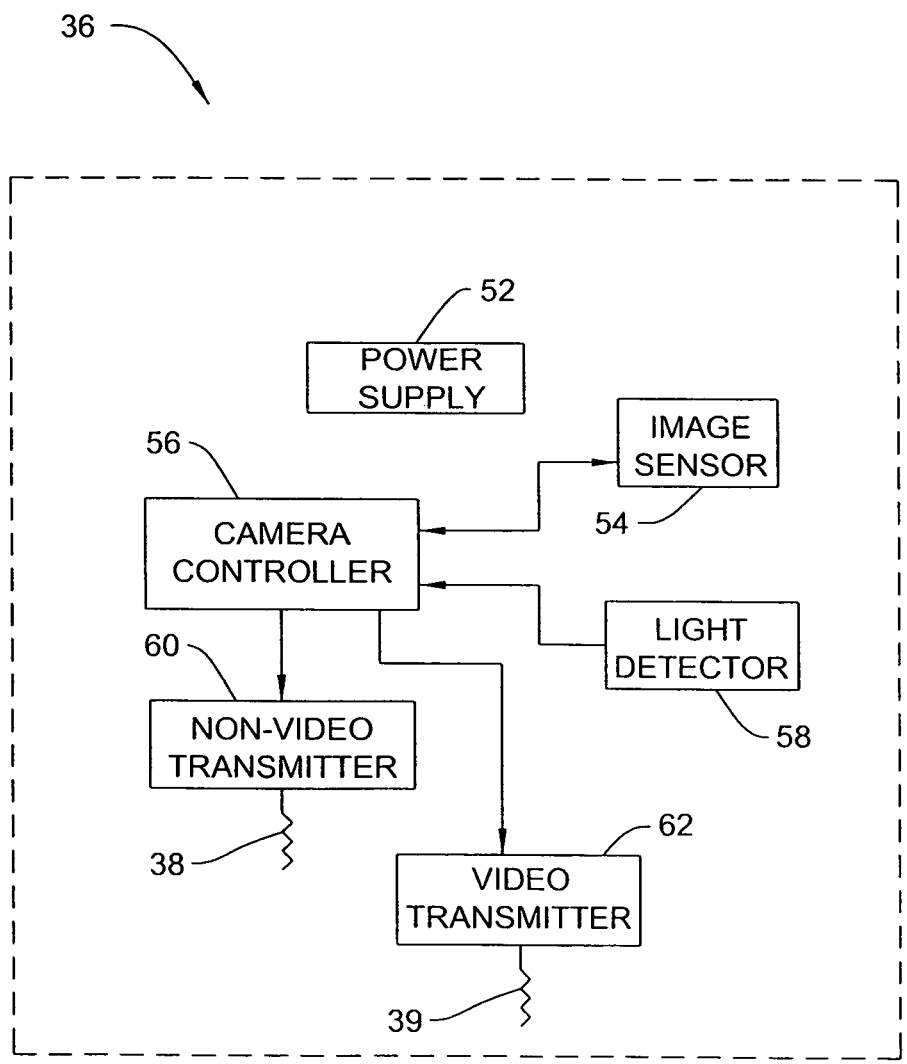
FIG. 2 is a block diagram of the video camera unit.

FIG. 2 is a block diagram of electrical components of the portable endoscopic video camera unit 36. A power supply or battery 52 provides power to the various electrical components. An image sensor 54 typically is located at a proximal end (not shown) of the video camera unit 36 for sensing images at surgical site 34. The image sensor 54 typically is a C-MOS sensor or a CCD sensor. The image sensor 54 provides a video image to a camera controller 56. A separate light detector 58, such as a photosensor, is provided near the image sensor 54 and is connected to the camera controller 56. The light detector 58 provides an output to the camera controller 56 so that the camera controller measures the specific time phase and time length of light output from the light source unit 40 that is received by the video camera unit 36. The camera controller 56 connects to a non-video camera unit transmitter 60 for transmitting light source control signals via transmitting antenna arrangement 38 to the light source unit 40. Further, the camera controller 56 includes a video transmitter 62 including the antenna arrangement 39. The video transmitter 62 transmits a wireless video signal from the camera controller 56 to a receiver (not shown) of the system controller 14 and/or to the video display 20. The wireless video and non-video signals are typically transmitted over different channels.

In another embodiment of the endoscopic video camera unit 36, a video cable 44 shown by broken line in FIG. 1, connects the video camera unit 36 to camera communication unit 46 also shown in broken line. In this embodiment, video image signals are sent via cable 44 to the camera communication unit 46. The camera communication unit 46 provides video signals to the system controller 14 and/or to the video display 20 over network 18 or over a dedicated cable (not shown). Further, a power cable (not shown) can be connected to the endoscopic video camera unit 36, in combination with the video cable 44. In this embodiment, the video camera unit 36 does not require battery 52 or wireless video transmitter 62.

Figure 3:
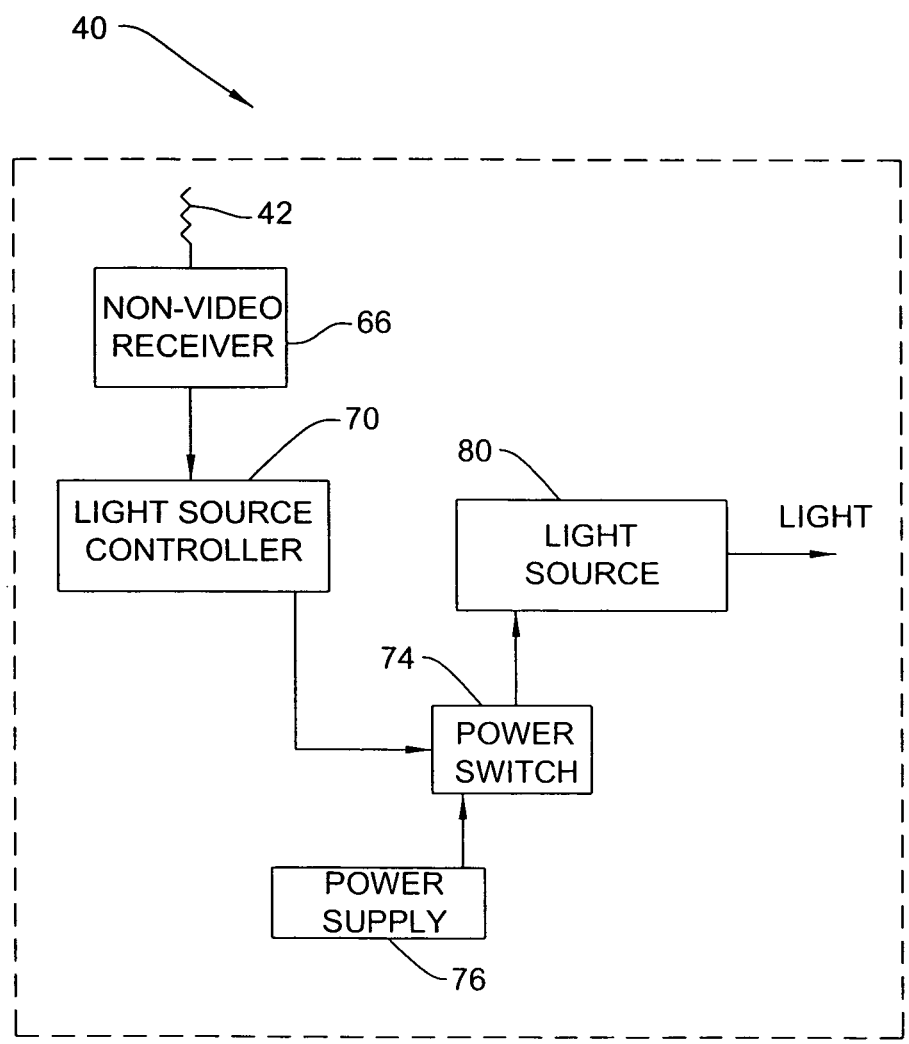
FIG. 3 is a block diagram of the light source unit.

FIG. 3 is a block diagram of the electrical components of the portable light source unit 40. The light source unit 40 includes a wireless signal receiving antenna arrangement 42. The receiving antenna arrangement 42 provides a received wireless control signal through a light source non-video receiver 66 to a light source controller 70. The light source controller 70 provides drive signals to a power switch 74. The power switch 74 typically is an electronic switching device or the like for permitting light source power supply or battery 76 to power a light source 80. Power supply 76 also provides operating power to the receiver 66 and light source controller 70.

With regard to the light source 80, one embodiment of the invention provides an LED array of R-G-B light output diodes. In another embodiment, the light source 80 includes an array of white light output diodes. In some embodiments, the light source includes an RGB rotary filter light source. Further, other light sources including various types of lamps are contemplated.

Synchronizing Operation—Message Packet Embodiment

In the camera control unit 36, high definition video signals are sensed by the image sensor 54 at a field rate of 0.0166 seconds corresponding to ⅟₆₀ of a second for NTSC signals (National Television Standards Committee). Thus, the camera shutter period S shown in FIG. 4 corresponds to about 0.0166 seconds in this embodiment.

Figure 4:
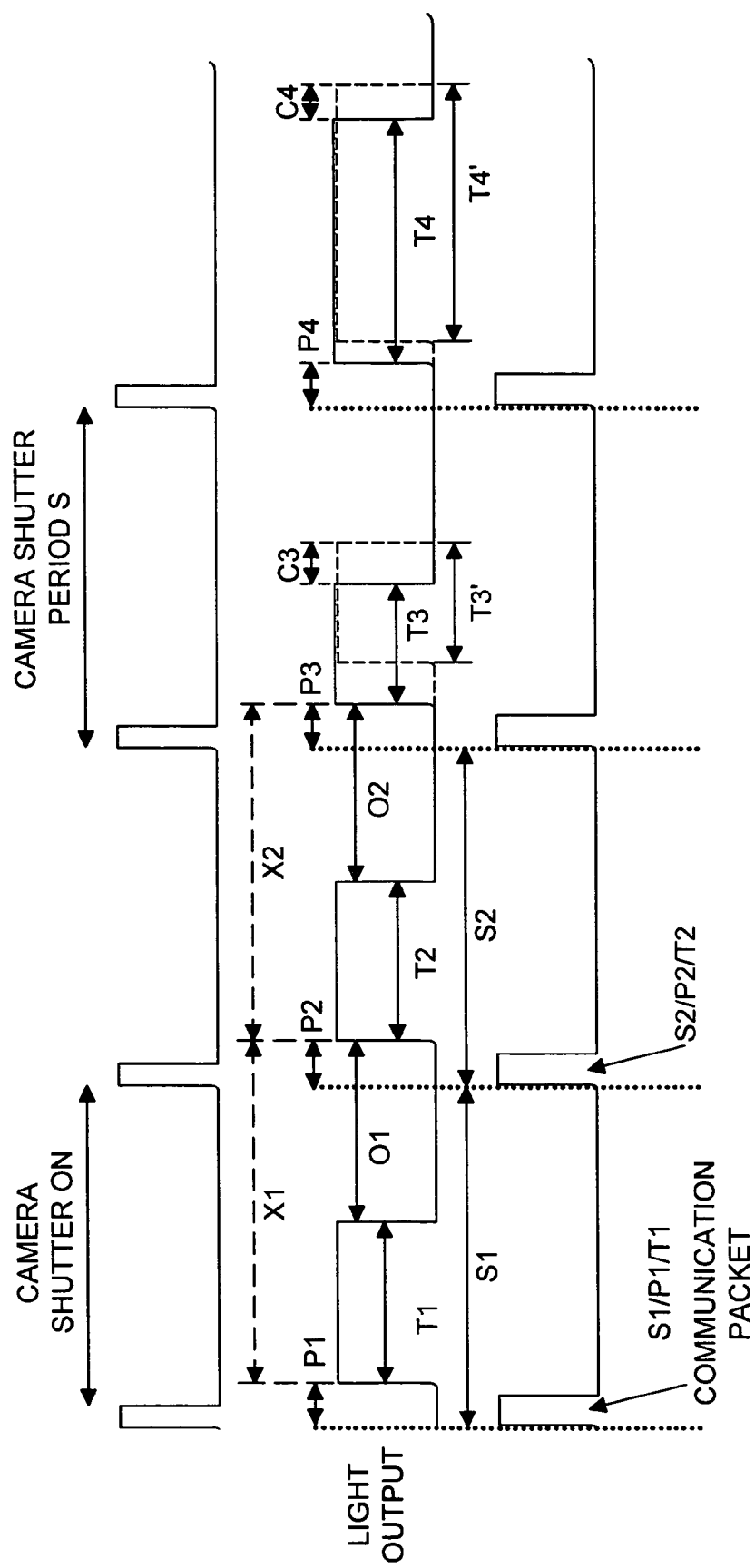
FIG. 4 is a graph of camera shutter operation, light source output and camera controller data communication versus time.

For the camera controller 56 to synchronize with the light source unit 40, small communication or message packets S/P/T as labeled in FIG. 4 are output by the non-video camera transmitter 60 periodically on a continuous RF carrier wave over a data channel. Each communication or message packet S/P/T has a duration from 100 nanoseconds (0.1 microseconds) or less, to one millisecond or more. The camera shutter period S shown in FIG. 4 includes a small time that the electronic shutter of the image sensor is closed or off for each image collecting period and a large camera shutter ON time that the electronic shutter is open to receive light and to collect an image from a surgical site 34.

As shown in FIG. 2, for synchronization the camera controller 56 transmits periodic message packets S/P/T via non-video transmitter 60 and antenna arrangement 38. The receiver antenna arrangement 42 shown in FIG. 3 provides the message packet S/P/T to light source non-video receiver 66 of the light source unit 40, which forwards the message packet S/P/T to light source controller 70. The light source controller 70 utilizes received target camera shutter period S for providing a reference value corresponding to the camera shutter period. The target camera shutter period S sets or corresponds to reference points represented by vertical dotted line in FIG. 4 for operation of the light source 80. Further, the message packet S/P/T includes a light source target phase P or time shift value to determine when to start illumination of the light source 80 relative to the reference point determined from the target camera shutter period S. The message packet also provides a light source target ON time T, such that the light source 80 operates for the length of time T after target phase P1.

Thus, in response to the message packet S1/P1/T1 shown in FIG. 4, the light source controller 70 controls power switch 74 for enabling power from battery 76 to power the light source 80 starting at the end of target phase P1 relative to camera shutter period S to illuminate the surgical site 34 for light source ON time T1. Message packets S/P/T repeat to sequentially control the light source 80 at desired target phases P for target ON times T.

In operation, the target shutter period S is representative of a time period for synchronization of a clock of the camera control unit 36 with a clock of the light source unit 40. If the value of target phase P has a constant value for each field or interval, the clocks of the units 36, 40 are at a fixed frequency relative to each other.

As illustrated in FIG. 4, the light source unit 40 sequentially outputs light for the respective light source target ON times T1, T2, T3, T4 at the end of respective target phases P1, P2, P3, P4. The value of the ON time T varies depending upon the amount of light required by image sensor 54 of the video camera unit 36 to obtain desired video images. Thus, in instances where the image sensor 54 requires more light to obtain a desired image, the ON time T is increased.

A closed-loop feedback type of arrangement is provided by the light detector 58 of the video camera unit 36. The light detector 58 senses the start-up time and the duration of light that is output from the light source 80 and provides a light output signal to the camera controller 56. In response to the actual measured start time (corresponding to the end of target phase P) and the actual measured light output duration (corresponding to light source ON time T), the camera controller 56 ensures that the value for a subsequent target phase P and the value for a subsequent target ON time T transmitted by camera transmitter 60 to the light source unit 40 result in a proper and synchronized light output. Further, small adjustments in the value of the target camera shutter period S are made as necessary to maintain a proper reference point. The synchronized closed-loop feedback arrangement ensures that light which is output from light source 80 only occurs during the time that the electronic camera shutter is on/open for each field. As shown in FIG. 4, the camera shutter ON time exceeds the light source ON time T that light is output by a significant amount. The additional time that the shutter is open is of no importance, as the surgical site 34 is not being illuminated by the light source 80.

In some embodiments, when the image sensor 54 of the video camera unit 36 is not powered while the video camera unit remains powered on, the camera controller 56 outputs an OFF message to the light source unit 40. The light source controller 70 ends operation of the light source 80 in response to the image sensor 54 not obtaining images.

In some embodiments, when the video camera unit 36 is not powered (turned OFF), message packets S/P/T are not sent and thus are not received by the light source unit 40. After a predetermined time without detecting a message packet, the light source unit 40 stops outputting light and automatically turns off.

In instances when the time duration of the message packet S/P/T is equal or greater than 1 millisecond, the received values S/P/T are used to control a subsequent operation of the light source 80 during the next camera shutter period S. For example, in the timeline shown in FIG. 4, the message packet S1/P1/T1 can control operation of the light source 80 in the camera shutter period that is currently labeled S2, P2, T2. The feedback through the light detector 58 and calculations by the camera controller 56 then account for the delay by one period or field.

As a result of the synchronization of the portable endoscopic video camera unit 36 and the portable endoscopic light source unit 40, the video camera unit operates to provide video signals to the video display 20. The camera controller 56 receives video images from image sensor 54 and provides video output signals to wireless video transmitter 62 to transmit the video signals directly to the video display 20 and/or to a video receiver of the system controller 14. One example of such a video camera output communication arrangement is disclosed in commonly owned U.S. PCT Application PCT/US09/005934 filed Oct. 30, 2009 and titled WIRELESS OPERATING ROOM COMMUNICATION SYSTEM INCLUDING VIDEO OUTPUT DEVICE AND VIDEO DISPLAY, which corresponds to Provisional Application Ser. No. 61/199,921, filed Nov. 21, 2008, the disclosures of which are hereby incorporated by reference herein.

While the above arrangement is described for an NTSC arrangement having ⅟₆₀$^{th}$ second per field, in another embodiment, the camera shutter period S and other features are based on a ⅟₅₀$^{th}$ second camera shutter period, such as for a PAL (Phase Alternating Line) arrangement.

In another embodiment of the invention, communication or message packets S/X/T are transmitted periodically from the video camera unit 36 on a continuous carrier wave. Target camera shutter period S and light source target ON time T are the same as discussed above. In this embodiment, "X" represents a light source target trigger time X having a start time referenced at the beginning of the ON time T of the light source 80. The target trigger time X has a time length or value corresponding to the ON time T and a subsequent off time for the light source 80. This target trigger time X ends at the next start ON time for the light source 80. In reference to FIG. 4, trigger time X1 equals S1+P2−P1. Thus, trigger time X1 begins at the end of the target phase P1 (beginning of light source output at target ON time T1) and continues until the end of target phase P2 (beginning of a second light source output at target ON time T2). In one embodiment, target trigger times X repeat for subsequent time periods.

In another embodiment, the S/X/T packet, after initial synchronization over target camera shutter period S, is capable of operating the video camera unit 36 by sending time values X/T as subsequent message packets, since target trigger time X is a target time that is referenced by the beginning of light source output and by subsequent start up time for a subsequent light source output. This embodiment utilizes the beginning of ON time of the light source 80, instead of the beginning of a camera shutter period S, as a reference point in time.

In another modification or embodiment, an initial value for the target trigger time X, based on the camera shutter period S, is calculated by the camera controller 56. Thus, the shutter period is not transmitted from the video camera unit 36 to the light source unit 40. Instead, only the target trigger time X and the target ON time T are transmitted to the light source unit 40.

The embodiments including target phase P and target trigger time X act to provide a target start for the beginning of a light source output.

In another embodiment, the target trigger time X is replaced by a target OFF time O as follows. The video camera controller 56, based in part on the shutter period S, calculates a target ON time T and a target OFF time O. Thus, the shutter period S is not transmitted from the video camera unit 36 to the light source unit 40. The target ON time, of course corresponds to the time that the light source 80 is ON. The target OFF time corresponds to the time the light source is off, before the next target ON time T. Thus the values target ON time T and target OFF time O are in sequential order.

Of course, all of the embodiments described above (S/X/T, X/T and T/O) are intended to operate with a closed-loop feedback type of arrangement provided by the light detector 58 of the video camera unit 36. As discussed above, the light detector 58 senses the start-up time and the duration of light output by the light source 80. The camera controller 56 utilizes this information, along with outputs from the image sensor 54 as needed, to calculate target values S/X/T, X/T or T/O for the various embodiments. The target values are then transmitted to the light source unit 40 for processing by the light source controller 70.

As discussed above with respect to the S/P/T embodiment, the values for the respective S/X/T, X/T and T/O embodiments can be transmitted as wireless data packets from the non-video transmitter 60 of the video camera unit 36 to the non-video receiver 66 of the light source unit 40.

The embodiments X/T and T/O, however, present difficulties for optical data transmission of information from the light source unit 40 to the video camera unit 36 as described below.

Optical Data Transmission

In another message packet embodiment, the light source unit 40 provides data or information to the video camera unit 36 via optical data transmission.

To send information from the light source unit 40, the light source controller 70 provides an additional predetermined target phase or time shift for operation of the light source 80. Instead of simply operating at the target phase P provided from the camera controller 56, an additional predetermined target phase or time shift is provided with a predetermined magnitude that corresponds to an individual data bit. The time shift or phase change at the beginning of the light output from light source 80 is detected by the light detector 58 of the video camera unit 36. The predetermined time shift or phase change is large enough that the camera controller 56 realizes a data bit has been sent, rather than simply a minimal error requiring correction by the next message packet to adjust the closed-loop system.

For example, as shown at the third camera shutter period T3 in FIG. 4, the beginning and the end of light source output ON time or interval T3 may be time shifted forward by a two microsecond time shift, or instead delayed by two microseconds C3 as shown in broken line corresponding to time interval T3' to provide a bit signal of "one". The two microsecond length of the time shift is large enough that the camera controller 56 realizes that a data bit has been transmitted, instead of a feedback error indicating that the light source 80 is not synchronized properly. The overall length of time T3, T3' of the light output does not change.

Transferring of a "zero" bit, signal is shown in the fourth camera shutter period of FIG. 4. A beginning of the light source output T4 can be shifted forward or can be delayed one microsecond C4 as shown in broken line corresponding to time interval T4' to provide a bit signal of "zero". The one microsecond time shift C4 is detected and recognized by the light source unit 40 as a "zero" bit. The overall length of time interval T4' that the light source 80 provides a light output does not change from the length of time interval T4.

After a detection of bit signal "one" from a time shift C3 during a first camera shutter period S or of bit signal "zero" from a time shift C4, the camera controller 56 adjusts the expected time values of the received signals from the light detector 58. Thus, the camera controller 56 adjusts the values S/P/T, as necessary, for sending a subsequent message packet that ignores the actual phase or time shift caused by the bit signals. The time shifts C3, C4 for the bit data need not be one microsecond or two microseconds. The time shift values C3, C4 must be large enough so that the camera controller 58 distinguishes the time shift from feedback error requiring correction. Further, the time shift values C3, C4 must not be so large that the light source 80 emits light during the camera shutter off portion of the camera shutter period S.

In the bit transfer arrangement, a sequence of bit values provide data or information to the camera controller 56 with regard to characteristics or conditions of the battery powered light source unit 40. Such data or information includes identifying the type of light source unit 40, remaining battery life for the light source battery 76, the amount of usage over the lifetime of the light source 80 including cumulative operating hours for LEDs of the light source, and the type of LEDs or lamp components provided for the light source 80. In some embodiments, the information is useful for determining the target ON time T required for driving the light source 80.

RF Signal Presence Embodiment

Figure 5:
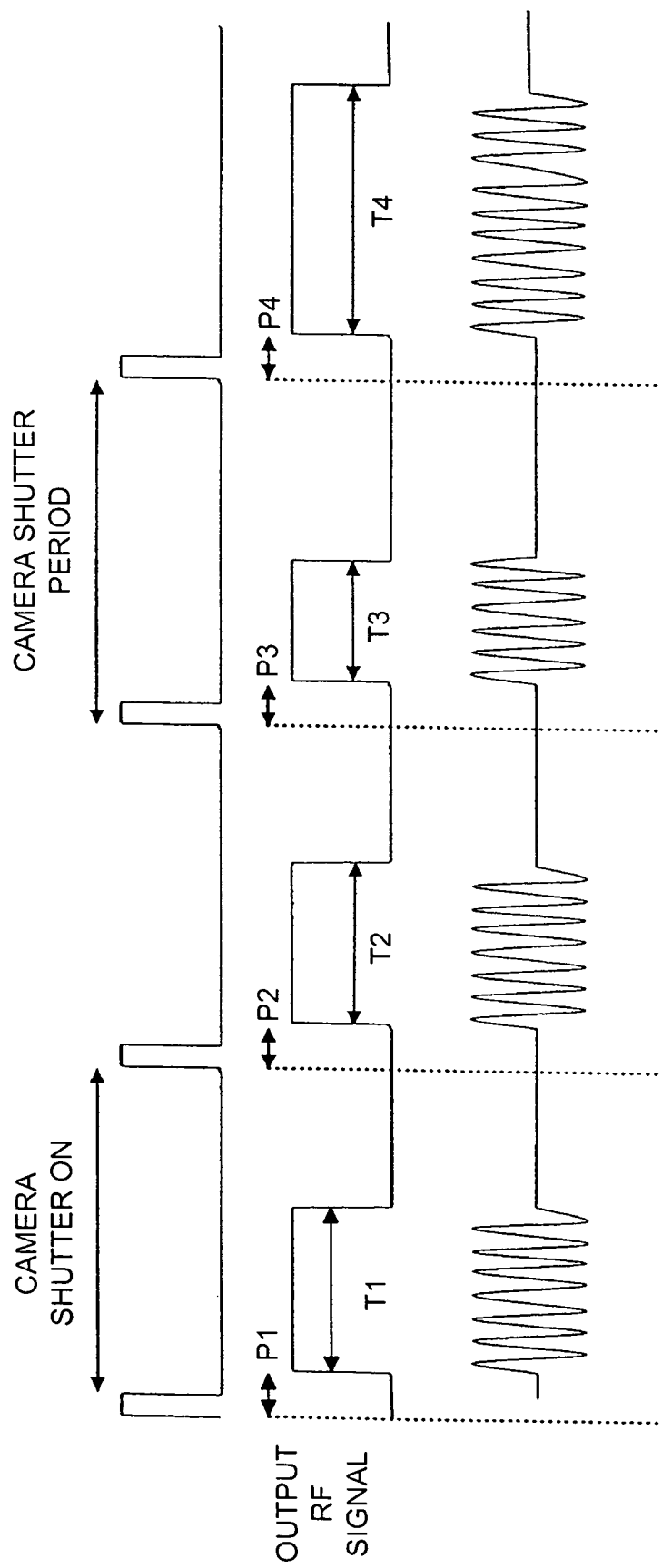
FIG. 5 is a graph of camera shutter operation, light source operation, and an RF signal for controlling light source operation versus time.

Another embodiment of the invention shown in the graph of FIG. 5 operates in a different manner to the message packet arrangement discussed above and illustrated in FIG. 4. The same type of light output feedback using light detector 58 and camera controller 56 as discussed above provides a closed-loop synchronization of the light source 80 of the endoscopic light source unit 40 with the endoscopic video camera unit 36.

In this embodiment, rather than sending a message packet S/P/T, the camera controller 56 provides a periodic or intermittent wireless RF signal via transmitter 60 and antenna arrangement 38. In this mark-space scheme, the light source ON time T is specified by the mere presence of the RF carrier signal. The RF signal is received by antenna arrangement 42 and non-video receiver 66.

As shown in FIG. 5, the presence of the RF carrier signal causes the light source controller 70 to actuate power switch 74 and provide battery power to the light source 80. The light source 80 provides a light output that is sensed by the light detector 58. When the RF signal is not detected, the light source unit 40 stops the light source 80 from outputting light. The synchronization system operates in a similar manner to the arrangement illustrated in FIG. 3, except that the resolution of control of the duration or ON time of the light source 80 is limited by the carrier frequency of the RF signal arrangement as the RF signal wave may be at a maximum or minimal value when the RF signal is first transmitted and received. Further, RF interference and noise may reduce the robustness of this RF signal embodiment.

In another embodiment, frequency shift keying (FSK) obtains the same result as the RF signal presence arrangement. A constant carrier signal is transmitted and frequency shift keying occurs during intervals T1, T2, T3, T4 shown in FIG. 5. The change or shift in frequency is easily detected by the light source controller 70. The detected frequency change enables operation of the light source 80 of the light source unit 40. Between ON times, the basic carrier frequency is received and essentially ignored by the light source controller 70.

Two-Way Wireless Communication Embodiment

Figure 6:
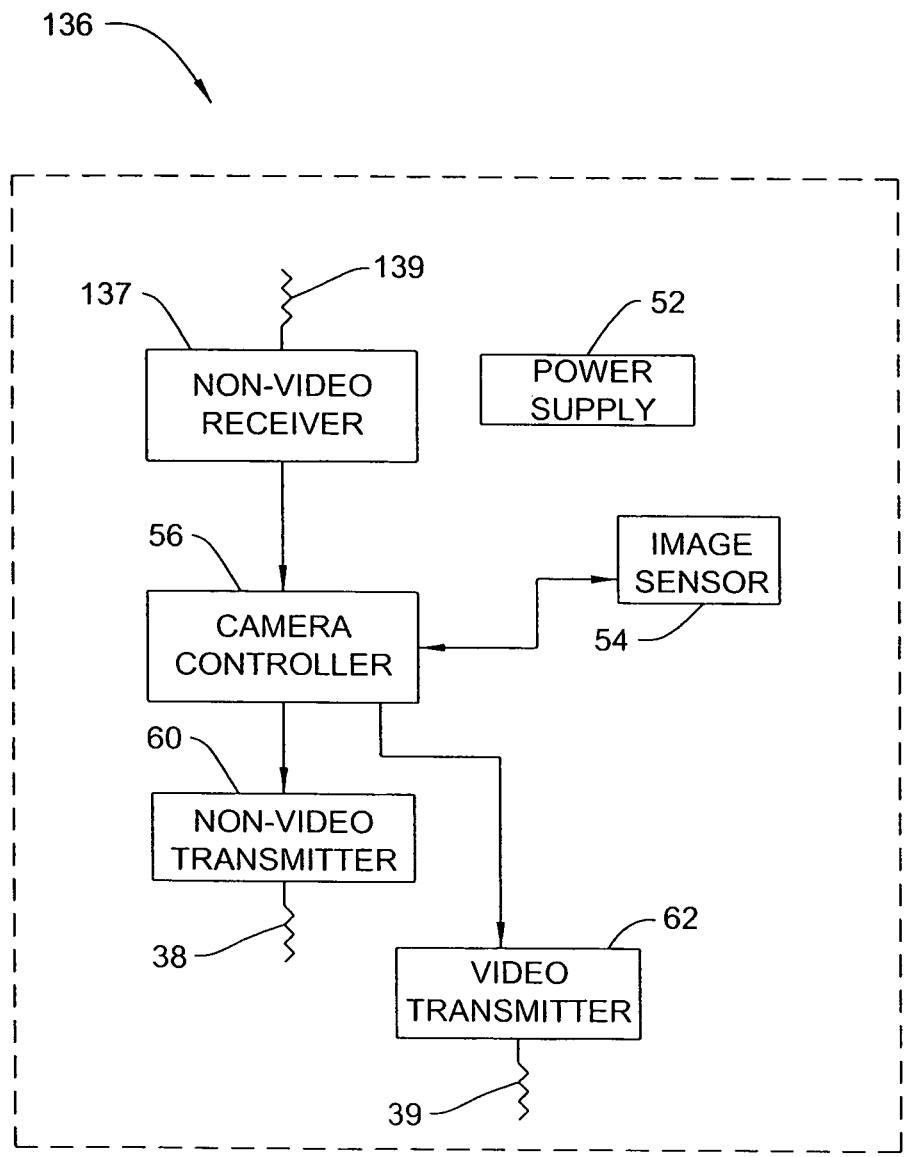
FIG. 6 is a block diagram of a second embodiment of the video camera unit.
Figure 7:
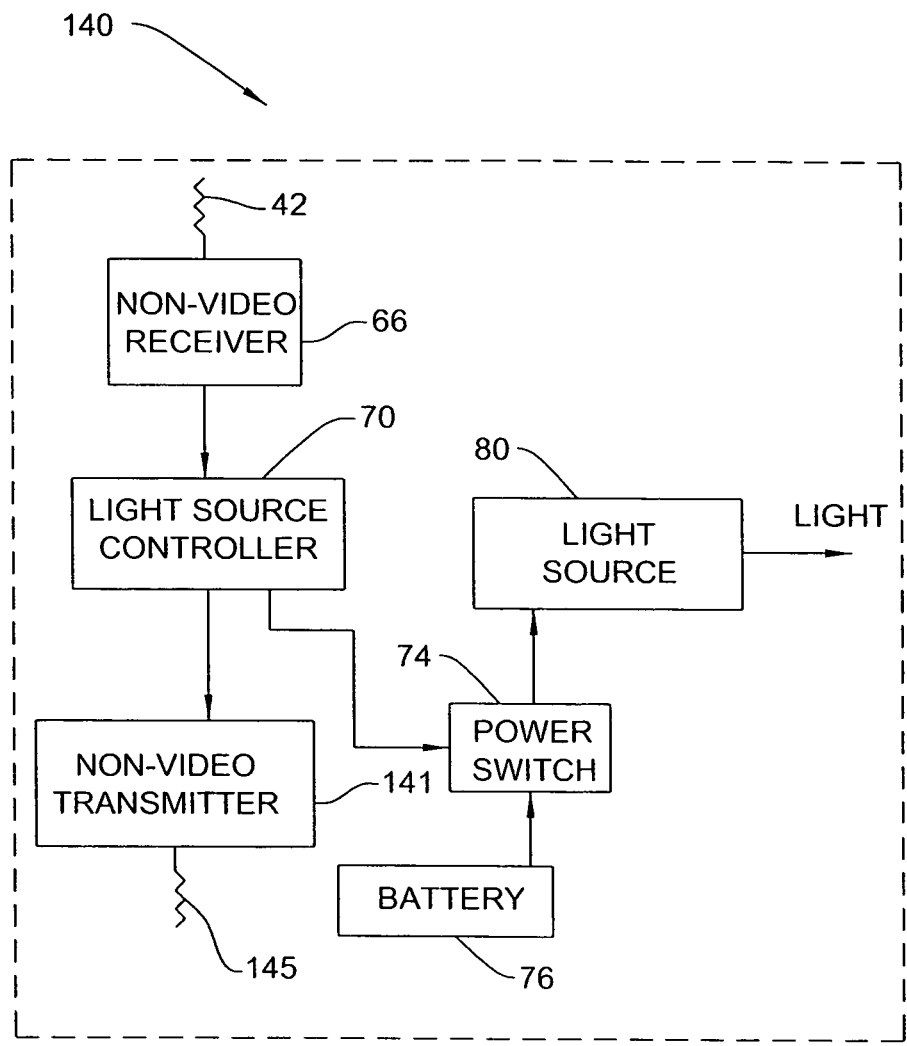
FIG. 7 is a block diagram of a second embodiment of the light source unit.

A two-way wireless communication embodiment includes a modified portable endoscopic video camera unit 136 as shown in FIG. 6 and a modified portable light source unit 140 as shown in FIG. 7. Components labeled in FIGS. 6 and 7 having the same reference numerals as presented in FIGS. 2 and 3 have essentially the same function.

The portable endoscopic video camera unit 136 shown in FIG. 6 includes a camera non-video receiver 137 with a camera non-video receiving antenna arrangement 139. No light detector, as such light detector 58, is provided in this embodiment.

The portable light source unit 140 shown in FIG. 7 is similar to the light source unit 40 shown in FIG. 3, except a wireless light source unit non-video transmitter 141 having a light source unit transmitting antenna arrangement 145 is provided.

In operation, the camera controller 56 transmits message packets S/P/T or S/X/T via non-video transmitter 60 and antenna arrangement 38 as discussed above with respect to FIG. 4. The non-video light source receiver 66 receives the wireless carrier signal having message packets from the camera transmitter 60 and provides the message packets S/P/T or S/X/T to the light source controller 70. The target camera shutter period S, target phase P/trigger time X and target ON time T are provided to the light source controller 70 for operation of the light source 80.

Instead of providing the video camera unit 136 with a separate light detector to assist in synchronizing the video camera unit and the light source unit 140 as discussed above with respect to FIG. 4, the two-way communication embodiment relies on light source wireless non-video transmitter 141 and antenna arrangement 145 to return a radio frequency signal, preferably with a return signal, such as a message packet, at a different time period within the same or a subsequent camera shutter period S through the receiving antenna arrangement 139 to the camera non-video receiver 137. The return message packet is used for synchronization and for data transmission purposes.

With regard to return data transmission, the light source controller 70 provides one or more data items on the return message packet that may include information regarding A) the type of light source 80, such as light-emitting diodes, B) the type of battery 76 provided with the light source unit 140, C) the battery charge time remaining, and D) the usage or hours that the light source 80 has been driven. Other information, such as the type of light source unit 136 can be provided.

In the two-way wireless arrangement, the exchange of RF signals with message packets acts to synchronize the video camera unit 136 and the portable endoscopic light source unit 140 so that the light source 80 outputs light only during the camera shutter ON portion of the camera shutter period S.

Further, in another two-way wireless arrangement, the message packets X/T and T/O are utilized. The send time of the message packet can be utilized as a reference point in time as necessary.

In some embodiments, the antenna arrangements 38, 39, 42, 139, 145 disclosed above are single antennas. In other embodiments, some of the antenna arrangements 38, 39, 42, 139, 145 are formed by a plurality of, or an array of antennas. In some embodiments, the antenna arrangements 38, 39 shown in FIG. 2 are provided as a combined or shared antenna. In some embodiments, the antenna arrangements 38, 39, 139 shown in FIG. 6 are provided as a shared antenna or antenna array. Finally, in some embodiments, the antenna arrangements 42, 145 shown in FIG. 7 are provided as a combined or shared antenna arrangement having one or a plurality of antennas.

In the embodiments discussed above, the light source 80 is intended to output light at a constant illumination value. In other embodiments, the light output level can be controlled or varied depending on the type of surgical procedure, the type of wireless video camera unit or other factors.

Although particular preferred embodiments of the invention are disclosed in detail for illustrative purposes, it will be recognized that variations or modifications of the disclosed method and apparatus, including the rearrangement of parts or steps, lie within the scope of the present invention.

What is claimed is:

1. Method of wirelessly synchronizing a camera shutter of an image sensor with operation of a light source for performing an endoscopic procedure comprising the steps of:

providing an endoscopic video camera unit including the camera shutter with the image sensor and a camera controller connected to a wireless non-video transmitter;

providing a portable light source unit including a light source controller connected to a wireless non-video receiver and to the light source;

determining a target camera shutter period and a light source target ON time with the video camera unit;

determining a light source target phase with the video camera unit;

transmitting the target camera shutter period, the light source target phase and the light source target ON time from the wireless non-video transmitter of the video camera unit to the wireless non-video receiver of the portable light source unit;

providing the target camera shutter period, the light source target phase and the light source target ON time from the wireless non-video receiver to the light source controller;

starting operation of the light source with the light source controller at a time defined by the light source target phase relative to a reference point in time defined by the target camera shutter period; and maintaining operation of the light source for the light source target ON time, wherein the steps of determining a target phase and determining a light source target ON time with the video camera unit comprises a closed loop feedback system that compares the light source target phase with the actual light source phase to calculate a new target phase and that compares the light source target ON time with the actual light source ON time to calculate a new light source target ON time.

2. The method according to claim 1, wherein the step of transmitting the target camera shutter period, the light source target phase and the light source target ON time from the wireless non-video transmitter of the video camera unit to the wireless non-video receiver of the light source unit comprises transmitting the target camera shutter period, the target phase and the target ON time as data within a message packet carried by a wireless RF signal.

3. Method of wirelessly synchronizing a camera shutter of an image sensor with operation of a light source for performing an endoscopic procedure comprising the steps of:

providing an endoscopic video camera unit including the image sensor and a camera controller connected to a wireless non-video transmitter;

providing a portable endoscopic light source unit including a light source controller connected to a wireless non-video receiver and to the light source;

determining a target camera shutter period and a light source target ON time with the video camera unit;

determining a light source target phase with the video camera unit;

transmitting the target camera shutter period, the light source target phase and the light source target ON time from the wireless non-video transmitter of the video camera unit to the wireless non-video receiver of the portable light source unit;

providing the target camera shutter period, the light source target phase and the light source target ON time from the wireless non-video receiver to the light source controller;

starting operation of the light source with the light source controller at a time defined by the light source target phase relative to a reference point in time defined by the target camera shutter period; and maintaining operation of the light source for the light source target ON time, providing the video camera unit with a light detector for measuring actual start time of light source operation and actual light source ON time for light output at a surgical site by the light source of the light source unit, wherein the steps of determining a target phase and determining a light source target ON time with the video camera unit comprises a closed loop feedback system that compares the light source target phase with the actual light source phase to calculate a new target phase and that compares the light source target ON time with the actual light source ON time to calculate a new light source target ON time.

4. The method according to claim 3, including the step of:

subsequently transmitting the new light source target phase and the new light source target ON time from the wireless non-video transmitter of the video camera unit to the wireless non-video receiver of the light source unit; and subsequently controlling the light source with the light source controller for starting the light source at a start time defined by the new target phase and for maintaining operation of the light source for the new light source target ON time.

5. The method according to claim 4, including the steps of:

transmitting data from the light source unit to the video camera unit by shifting the actual light source phase of the light output from the light source by a predetermined time shift; and wherein the step of determining a target phase and a target ON time with the video camera unit includes the steps of:

determining that a time shift in the actual light source phase indicates the presence of a bit value;

storing the bit value for evaluation; and re-adjusting the actual light source phase to account for the change in phase due to the time shift corresponding to a bit value before determining a subsequent new light source target phase and a subsequent new light source target ON time.

6. The method according to claim 5, wherein a sequence of bit values provides information from the light source unit to the video camera unit regarding at least one of: type of light emitting diodes provided for the light source; type of light source battery for the light source unit; remaining usage life for the light emitting diodes; driven hours for the light emitting diodes; and remaining charge hours for the light source battery.

7. Method of wirelessly synchronizing a camera shutter of an image sensor with operation of a light source for performing an endoscopic procedure comprising the steps of:

providing an endoscopic video camera unit including the image sensor and a camera controller connected to a wireless non-video transmitter;

providing a portable endoscopic light source unit including a light source controller connected to a wireless non-video receiver and to the light source;

determining a target camera shutter period and a light source target ON time with the video camera unit;

determining a light source target phase with the video camera unit;

transmitting the target camera shutter period, the light source target phase and the light source target ON time from the wireless non-video transmitter of the video camera unit to the wireless non-video receiver of the portable light source unit;

providing the target camera shutter period, the light source target phase and the light source target ON time from the wireless non-video receiver to the light source controller;

starting operation of the light source with the light source controller at a time defined by the light source target phase relative to a reference point in time defined by the target camera shutter period;

maintaining operation of the light source for the light source target ON time;

transmitting a light OFF signal from the wireless non-video transmitter of the video camera unit when the camera unit is no longer collecting video images;

receiving the light OFF signal at the light source unit; and discontinuing actuation of the light source so long as the video camera unit is not collecting and transmitting video signals.

* * * * *